United States Patent

Olesen et al.

Patent Number: 6,022,868
Date of Patent: Feb. 8, 2000

[54] SUBSTITUTED AZACYCLIC OR AZABICYCLIC COMPOUNDS

[75] Inventors: Preben Houlberg Olesen, Copenhagen; John Bondo Hansen, Jyderup, both of Denmark

[73] Assignee: Novo Nordisk Als, Bagsvaerd, Denmark

[21] Appl. No.: 08/973,847

[22] PCT Filed: Jun. 28, 1996

[86] PCT No.: PCT/DK96/00292

§ 371 Date: Dec. 19, 1997

§ 102(e) Date: Dec. 19, 1997

[87] PCT Pub. No.: WO97/01556

PCT Pub. Date: Jan. 16, 1997

[30] Foreign Application Priority Data

Jun. 29, 1995 [DK] Denmark .................. 0756/95

[51] Int. Cl.[7] ............ C07D 413/06; A61K 31/445
[52] U.S. Cl. .................. 514/210; 514/212; 514/326; 514/378; 540/602; 540/603; 546/209; 546/210; 546/211; 546/212; 548/134; 548/135; 548/128; 548/129; 548/143; 548/144; 548/131; 548/132; 548/183; 548/184; 548/188; 548/190; 548/191; 548/206; 548/213; 548/214; 548/247; 548/248; 548/252; 548/250; 548/255; 548/263.2; 548/262.2; 548/314.7; 548/950
[58] Field of Search .................. 540/602, 603; 546/209, 210, 211, 212; 548/128, 129, 134, 135, 131, 132, 143, 144, 183, 184, 188, 190, 191, 206, 213, 214, 247, 248, 252, 250, 263.2, 262.2, 314.7, 950; 514/210, 212, 326, 378

[56] References Cited

FOREIGN PATENT DOCUMENTS

0330353 A1   8/1989   European Pat. Off. .
0414394 A2   2/1991   European Pat. Off. .
WO 93/12108  6/1993   WIPO .

OTHER PUBLICATIONS

Chemical Abstracts, vol. 110, No. 16, The Abstract No. 135678n, p. 761., 1989.
Helak, B. et al., J. Agric. Food Chem., vol. 37, pp. 405–410 (1989).

*Primary Examiner*—Mukund J. Shah
*Assistant Examiner*—Deepak R. Rao
*Attorney, Agent, or Firm*—Steve T. Zelson; Carol E. Rozek

[57] ABSTRACT

Disclosed are compounds of formula (I) selected from the following

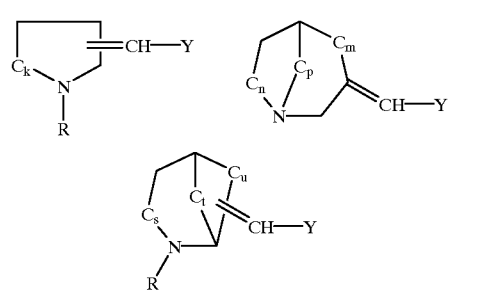

wherein Y is

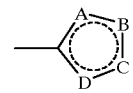

and wherein A, B, C, D, R, k, m, n, o, p, s, t and u are as defined in the specification. These compounds are useful in treating diseases in the central nervous system related to malfunctioning of the nicotinic cholinergic system.

10 Claims, No Drawings

SUBSTITUTED AZACYCLIC OR AZABICYCLIC COMPOUNDS

CROSS-REFERENCE TO RELATED APPLICATIONS

This application is a 35 U.S.C. 371 national application of PCT/DK96/00292 filed Jun. 28, 1996 and claims priority under 35 U.S.C. 119 of Danish application 0756/95 filed Jun. 29, 1995, the contents of which are fully incorporated herein by reference.

FIELD OF THE INVENTION

The present invention relates to heterocyclic compounds which are cholinergic ligands selective for neuronal nicotinic channel receptors, to methods for their preparation, to pharmaceutical compositions comprising them, and to their use in treating cognitive, neurological and mental disorders, which are characterized by decreased nicotine cholinergic function. The invention also relates to a method of treating Parkinson's disease by modulating the process of dopamine secretion, a method of treating or preventing withdrawal symptoms caused by cessation of chronic or long term use of tobacco products, as well as a method for treating obesity.

BACKGROUND OF THE INVENTION

Nicotinic and muscarinic receptors are the two distinct types of cholinergic receptors named after their selectivity for muscarine and nicotine, respectively. The cholinergic system is the neurotransmitter system that best correlates with memory and cognitive functions. Traditionally, the cholinergic hypothesis for senile dementia of the Alzheimer type (SDAT) has focused on muscarinic acetylcholine receptors (mAChR), and only recently an interest in the role of the nicotinic acetylcholine receptors (nAChR) in SDAT has emerged. This interest was spurred by the relatively recent discovery that nAChR are not only located on the skeletal muscle but also in the brain.

It has been shown that the number of nAChR were decreased in SDAT patients (Nordberg et al., J. Neurosci. Res.Vol. 31, pp. 103–111 (1992); Giacobini, Advances in Experimental Medicine and Biology, Vol. 296, pp.9205–9295, (1993); Schroeder et al., Neurobiol. of Aging, Vol. 12, pp. 259–262, (1991); Whitehouse et al., Neurology, Vol. 38, pp. 720–723, (1988); Flynn and Mash, J. Neurochem., Vol. 47, pp. 8702–8702, (1993)). Similar deficiencies in choline acetyltransferase activity and acetylcholine synthesis suggest that presynaptic receptors on cholinergic nerve terminals are preferentially lost in SDAT (Nordberg, J. Reprod. Fert. Suppl., Vol 46, pp. 145–154, (1993)). Therefore, it has been assumed that the loss of nAChR may correlate with age related onset of disorders of memory and cognitive functions, and that nicotinic replacement therapy may prove beneficial in SDAT. Indeed nicotine improved attention and memory in healthy humans (Warburton, Prog. Neuro. Psychopharmacol. Biol. Psychiatry, Vol. 16, pp. 181–191, (1992)) as well as in Alzheimer's disease patients, (Jones et al., Psychopharmacology, Vol. 108, pp. 485–494, (1992); Gitelman and Prohovnik, Neurobiol. of Aging, Vol. 13, pp. 313–318, (1992); Newhouse et al., Psychopharmacology, Vol. 95, pp. 171–175, (1988); Sahakian et al., Br. J. Psychiatry, Vol.154, pp. 9004–904, (1993)). Further the nicotinic antagonist mecamylamine has been shown to cause cognitive impairment in an age related way, (Newhouse et al., Neuropsychopharmacology, Vol 10, pp. 93–107, (1994)).

Parkinson's disease (PD) is a debilitating neurodegenerative disease, presently of unknown etiology, characterized by tremors and muscular rigidity. There is evidence that nicotine may also have beneficial effects in PD. Studies show that smoking may protect against the development of PD, (Ishikawa and Mmiyatake, J. Neurol. Sci., Vol. 117, pp. 28–32, (1993); Godwin-Austen et al., J. Neurol. Neurosurg. Psychiat., Vol. 45, pp. 577–581, (1982); Reavill, in Nicotine psychopharmacology: Molecular, cellular and behavioral aspects, pp. 307–340, Oxford University Press, (1990)), and that chronic nicotine may protect against cell loss in the substantia nigra caused by lesioning (Janson and Moller, Neuroscience, Vol. 57, 931–941, (1993)). Nicotine has also shown beneficial effects in Tourette's syndrome (Sanberg et al., Biomed. Phamacother., Vol. 43, pp. 19–23, (1989)). Alleviation of negative psychotic symptoms, known as the hypofrontality syndrome in schizophrenia, by nicotinic agonists, have been suggested by data showing that nicotine stimulates dopamine release in the nucleus accumbens more potently than in striatum, (Rowell et al. J. Neurochem., Vol. 49, pp. 1449–1454, (1987); Giorguieff-Chesselet et al., Life Sciences, Vol. 25, pp. 1257–1262, (1979)), by nicotinic reversal of inactivation of prefrontal neurons (Svenson et al., In the Biology of Nicotine dependence., pp. 169–185, New York, (1990)), and by the observation that nicotine will potentiate dopaminergic effects in various behavioral models, (Reavill, in Nicotine psychopharmacology: Molecular, cellular and behavioral aspects, pp. 307–340, Oxford University Press, (1990); Rosecrans et al., Psychopharmacol. Commmun., Vol. 2, pp. 349–356, (1976); Reavill and Stolerman, J. Psychopharmacol., Vol. 1, pp. 264, (1987)).

In recent years there have been several studies on the effects of nicotine and food consumption and associated changes in body weight in rat and human. (Greenberg et al., Addictive behaviours, Vol. 7, pp. 317–331, (1982) and Greenberg et al., Psychopharmacology, Vol. 90, pp. 101–105, (1984)). The appetite effects of nicotine have been suggested to be mediated via modulation of CCK peptides in the paraventricular hypothalamic nucleus (Fuxe et al., Acta Physiologica Scandinavica, Vol. 125, pp. 437–443, (1985)).

EP 414394 discloses a class of methyleneazabicyclic compounds, substituted with a five membered heterocyclic ring described as cholinergic compounds which enhance acetylcholine function via an action at muscarinic receptors within the central nervous system.

DESCRIPTION OF THE INVENTION

It is an object of the invention to provide compounds with affinity and selectivity for nicotinic cholinergic receptors, to methods for their preparation, to pharmaceutical compositions containing them, and to their use in treating Alzheimer's disease, Parkinson's disease, Tourette's syndrome, ulcerative colitis, obesity, other central nervous system and gastrointestinal disorders as well as severe pain.

The present invention relates to novel substituted azacyclic or azabicyclic compounds of formula I selected from the following:

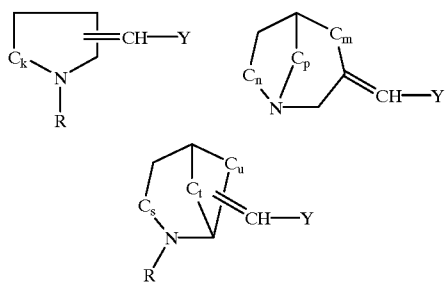

(I)

wherein k is 0, 1, 2 or 3; and
m is 0 and p is 2 and n is 2, or m is 1 and p is 1 and n is 2, or m is 0 and
p is 1 and n is 0; and
s is 0, 1 or 2; and
t is 1 or 2; and
u is 1, 2 or 3; and
R is hydrogen, $C_{1-6}$-alkyl or $C_{3-6}$-cycloalkyl; and
wherein Y is

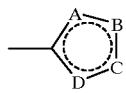

wherein —A—B—C—D— is selected from =C($R^1$)—O—N =C($R^2$)—, =C($R^1$)—S—N =C($R^2$)—=C($R^1$)—N =C($R^2$)—O—, =C($R^1$)—C($R^2$)=C($R^3$)——, =C($R^1$)—C($R^2$)=N—C—, =C($R^1$)—N =C($R^2$)—S—, =C($R^1$)—C($R^2$)=C($R^3$)—S—, =C($R^1$)—C($R^2$)=N—S—, —C($R^1$)=C($R^2$)——C($R^3$)=—C($R^1$)=C($R^2$)—S—C($R^3$)=, —N($R^4$)—N =C($R^1$)—C($R^2$)=, =N—N($R^4$)—C($R^1$)=C($R^2$)——=N—O—C($R^1$)=C($R^2$)—, =N—S—C($R^1$)=C($R^2$)—, —N($R^4$)—C($R^1$)=N—C($R^2$)=,—N =C($R^1$)—N($R^4$)—C($R^2$)=, =C($R^1$)—N ($R^4$)—N =C($R^2$), —N =C($R^1$)—O—C($R^2$)=,—N =C($R^1$)—S—C($R^2$)==N—C($R^1$)=C($R^2$)—N ($R^4$)—, =N—C($R^1$)=C($R^2$)—O—, =N—C($R^1$)=C($R^2$)—S—, —N($R^4$)—N =N—C($R^1$)=, =N—N ($R^4$)—N =C($R^1$)—, —N =N—N($R^4$)—C($R^1$) —N($R^4$)—N =C($R^1$)—N==N—N($R^4$)—C($R^1$) =N—, =N—N =C($R^1$)—N($R^4$)—, =N—O—N =C($R^1$)—, =N—N =C($R^1$)—O—, —N =C($R^1$)—O—N=,=N—C($R^1$)=N—O—, =N—N =C($R^1$)—S—, =N—S—N =C($R^1$)—, =N—C(R)=N—S—, —N =C($R^1$)—S—N =, —N($R^4$)—N =N—N =, =N—N($R^4$)—N =N—; and $R^1$, $R^2$ and $R^3$ independently are hydrogen, halogen, —$NO_2$, —CN, —$NR^5R^6$, —$OR^7$, —$COOR^9$, —$SOR^{10}$, —$SO_2R^{11}$, —$SO_3R^{12}_1$ $C_{1-6}$-alkyl optionally substituted with one, two or three fluorine atoms, $C_{2-6}$-alkenyl, $C_{2-6}$-alkynyl, $C_{3-6}$-cycloalkyl, —$R^{13}$—O—$R^{14}$ or —$R^{15}$—S—$R^{16}$, and $R^4$ is $C_{1-6}$—alkyl, $C_{2-6}$—alkenyl, $C_{2-6}$——alkynyl, $C_{3-6}$—cycloalkyl, —$R^{17}$—O—$R^{18}$ or —$R^{19}$—S—$R^{20}$, wherein $R^5$ and $R^6$ independently are hydrogen, $C_{3-6}$—alkyl, $C_{2-6}$—alkenyl or $C_{2-6}$—alkynyl and wherein $R^7$, $R^8$, $R^9$, $R^{10}$, $R^{11}$, $R^{12}$, $R^{14}R^{16}$, $R^{18}$ and $R^{20}$ independently are hydrogen, $C_{1-6}$-alkyl, $C_{2-6}$-alkenyl, $C_{2-6}$-alkynyl or $C_{3-7}$-cycloalkyl and wherein $R^{13}$, $R^{15}$, $R^{17}$ and $R^{19}$ independently are $C_{1-6}$-alkylene, $C_{2-6}$-alkenylene or $C_{2-6}$-alkynylene; or a pharmaceutically acceptable salt thereof.

In a preferred embodiment the compounds of the invention is selected from compounds of formula I*a*

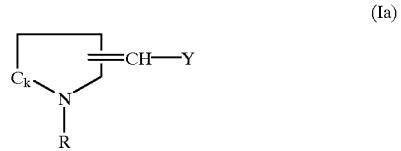

(Ia)

wherein A—B—C—D is selected from
=C($R^1$)—C($R^2$)=N—O—, =C($R^1$)—C($R^2$)=N—S—, =N—O—C($R^1$)=C($R^2$)—,
=N—S—C($R^1$)=C($R^2$)—, since these compounds have a preferred selectivity for nicotinic receptors as compared to muscarinic receptors.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically acceptable inorganic or organic acid addition salts, and include the pharmaceutically acceptable salts listed in Journal of Pharmaceutical Science, 66, 2 (1977) which are hereby incorporated by reference.

The compounds of formula I may exist as geometric and optical isomers and all isomers and mixtures thereof are included herein. Isomers may be separated by means of standard methods such as chromatographic techniques or fractional crystallization of suitable salts.

Alkyl, alkenyl and alkynyl as used herein mean straight or branched alkyl, alkenyl or alkynyl chains.

The invention also relates to a method of preparing the above mentioned compounds of formula I. These methods comprise:

a) reacting a compound of formula II selected from the following:

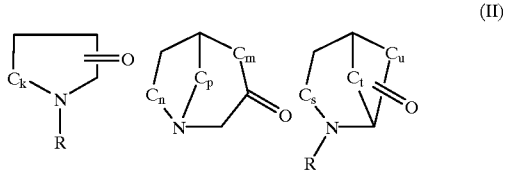

(II)

wherein R, k, m, n, p, s, t and u have the meanings defined above with a phosphorus ylide of formula III or a phosphonate of formula IV

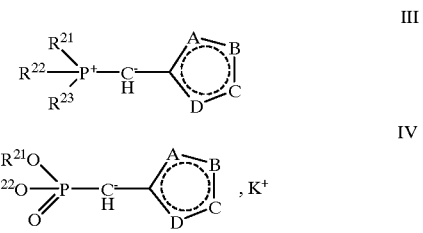

III

IV wherein $R^{21}$, $R^{22}$ and $R^{23}$ independently are $C_{1-6}$-alkyl, aryl or aralkyl and —A—B—C—D—has the meaning defined above, to give a compound of formula I; or b) reacting a compound of formula II with a compound of formula V

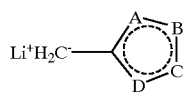

wherein —A—B—C—D— has the meaning defined above, followed by a dehydration to give a compound of formula I; or c) reacting a compound of formula II with a compound of formula VI

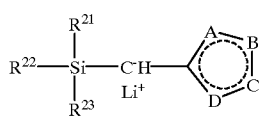

wherein $R^{21}$, $R^{22}$ and $R^{23}$ have the meanings defined above, to give a compound of formula I; or d) reacting a compound of formula II with a compound of formula VII

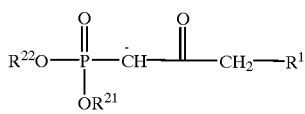

wherein $R^1$, $R^{21}$ and $R^{22}$ have the meanings defined above, to give a compound of formula VIII

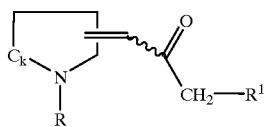

followed by reaction with dimethylformamide dimethylacetale and cyclization with hydroxylamine to give a compound of formula IX

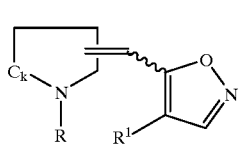

wherein R and $R^1$ have the meanings defined above.

The pharmacological properties of the compounds of the invention can be illustrated by determining their capability to inhibit the specific binding of $^3$H-methylcarbamylcholine ($^3$H-MCC) (Abood and Grassi, Biochem. Pharmacol., Vol. 35, pp. 4199–4202, (1986)).

$^3$H-MCC labels the nicotinic receptors in the CNS. The inhibitory effect on $^3$H-MCC binding reflects the affinity for nicotinic acetylcholine receptors.

Fresh or frozen rat, brain tissue (hippocampus or cortex) was homogenized in assay buffer (50mM Tris—HCI, pH 7.4, 120 mM NaCl, 5 mM KCI, 2 mM $CaCl_2$, 1mM $MgCl_2$) and centrifuged for 10 min. at 40.000×g. Pellets were subsequently reconstituted in assay buffer and an appropriate amount of tissue sample was mixed in tubes with $^3$H—methylcarbamylcholine (NEN, NET—951; final concentration 2 nM) and test drug. The tubes were incubated at 0° C. for 60 min. Unbound ligand was separated from bound ligand by vacuum filtration through GF/B filters presoaked in 0.5 % polyethylenimine. Filters were washed three times with 5 ml wash buffer (50mM Tris—HCI, pH 7.4) and transferred to vials. 4 ml scintillation fluid was added and the radioactivity was measured by scintillation counting. Unspecific binding was measured with 10 μM nicotine.

The $IC_{50}$ values of the test compounds were determined by nonlinear regression analyses (GraphPad InPlot).

Furthermore, the pharmacological properties of the compounds of the invention can also be illustrated by determining their capability to inhibit the specific binding of $^3$H-Oxotremorine—M ($^3$H-Oxo). Birdsdall N.J.M., Hulme E.C., and Burgen A.S.V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H—Oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 ml 20 mM Hepes pH: 7.4, with an Ultra—Turrax homogenizer. The homogenizer is rinsed with 10 ml of buffer and the combined suspension centrifuged for 15 min. at 40,000×g. The pellet is washed three times with buffer. In each step the pellet is homogenized as before in 2×10 ml of buffer and centrifuged for 10 min. at 40,000×g.

The final pellet is homogenized in 20 mM Hepes pH: 7.4 (100 ml per g of original tissue) and used for binding assay. Aliquots of 0.5 ml is added 25 ul of test solution and 25 ul of $^3$H-Oxotremorine (1.0 nM, final concentration) mixed and incubated for 30 min. at 25° C. Non-specific binding is determined in triplicate using arecoline (1 ug/ml, final concentration) as the test substance. After incubation samples are added 5 ml of ice-cold buffer and poured directly onto Whatman GFIC glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steam-bath for less than 5 min.) at a concentration of 2.2 mg/ml. 25–75% inhibition of specific binding must be obtained before calculation of $IC_{50}$. The test value will be given as $IC_{50}$ (the concentration (nM) of the test substance which inhibits the specific binding of $^3$H-Oxo by 50%).

$IC_{50}$=(applied test substance concentration) x$(C_x/C_o-C_x)$ nM where $C_o$ is specific binding in control assays and $C_x$ is the specific binding in the test assay. (The calculations assume normal mass-action kinetics).

Table I illustrates the affinity of the compounds of the present invention for nicotinic and muscarinic receptors as determined by $^3$H-MCC and $^3$H-Oxo binding to rat cortical receptors. The compounds, however, show selective affinity for nicotinic receptors as compared to muscarinic receptors, i.e OXO/MCC >1.

TABLE 1

| Compound | $^3$H-MCC IC$_{50}$ nM | $^3$H-Oxo IC$_{50}$ nM | Oxo/MCC Ratio |
|---|---|---|---|
| 1 | 3050 | 5150 | 1.7 |
| 5 | 100 | 10000 | 100 |

The compounds of the invention are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from diseases in the central nervous system caused by malfunctioning of the nicotinic cholinergic system it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intraurethral, intramuscular, topical, intranasal, ophthalmic solution or an ointment, the oral route being preferred.

Typical compositions include a compound of formula I or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

The invention will now be described in further detail with reference to the following examples:

EXAMPLE 1

3-Hydroxy-3-(3-methyl-5-isoxazolyl) methyl-1-methylpiperidine

To a solution of 3,5-dimethylisoxazol (4.86 g, 50 mmol) in dry tetrahydrofuran (15 ml) cooled to −78° C was added butyllithium (2.5 M in hexane, 50 mmol). The reaction mixture was stirred for 0.5 h. 1-methyl-piperidin-3-one (2.70 g, 23.9 mmol) dissolved in tetrahydrofuran (25 ml) was added. The reaction mixture was stirred for another 2 h at −78° C. Water (50 ml) was added and the reaction mixture was acidified with concentrated hydrochloric acid. The water phase was extracted with ether (2×50 ml), then made alkaline with potassium carbonate and extracted with methylene chloride (4×50 ml). The combined methylene chloride phases were dried over magnesium sulphate and evaporated giving the title compound in 4.18 g (83%) yield.

(Z)-3-(3-Methyl-5-isoxazolyl)methylene-1-methylpiperidine oxalate and 3-(3-methyl-5-isoxazolyl) methyl-1 -methyl-1 ,2,5, 6-tetrahydropyridine oxalate To a solution of 3-hydroxy-3-(3-methyl-5-isoxazolyl) methyl-i-methylpiperidine (1.5 g, 7.2 mmol) in methylene chloride (50 ml) thionylchloride (2.56 g, 21.5 mmol) was added. The reaction mixture was stirred overnight at room temperature. Water was added and the reaction mixture acidified with concentrated hydrochloric acid. The phases were separated and the water phase basified with potassium carbonate. The water phase was extracted with ether (3×50 ml). The combined ether extracts were dried over magnesium sulphate and evaporated. The crude compounds were separated by column chromatography (eluent: methylene chloride/methanol: 9/1). The first fractions contained (Z)-3-(3-methyl-5-isoxazolyl)methylene-1-methylpiperidine which was crystallized as the oxalate salt in 40 mg (3% yield). M.p. 163–164° C. (Compound 1). The next fractions contained 3-(3-methyl-5-isoxazolyl)methyl-1 -methyl-1,2,5, 6-tetrahydropyridine, which was crystallized as the fumarate salt in 240 mg (18% yield). M.p. 145–146° C. (Compound 2).

In exactly the same manner the following compounds were prepared:

4-(3-Methyl-5-isoxazolyl)methylene-1-methylpiperidine oxalate from 1-methylpiperidin-4-one and 3,5-dimethylisoxazole. M.p. 144–1 45° C. (Compound 3).

4-(3-Methyl-5-isoxazolyl) methyl-1 ,2, 5, 6-tetrahydro-1 -methylpiperidine oxalate from 1-methylpiperidin-4-one and 3,5-dimethylisoxazole. M.p. 127–128° C. (Compound 4).

EXAMPLE 2

(Z)-3-(3-Methyl-5-isoxazolyl)methylenepiperidine hydrochloride

To a solution of (Z)-3-(3-methyl-5-isoxazolyl)methylene-1-methylpiperidine (1.3 g, 6.5 mmol) in toluene (50 ml) was added 1-chloroethylchloroformate (1.3 g, 10 mmol). The reaction mixture was heated at reflux for 5 h. The reaction mixture was evaporated and methanol (50 ml) was added. The reaction mixture was heated at reflux for 1 h and evaporated. The crude compound was purified by column chromatography (eluent: methylene chloride/methanol/ammonium hydroxide (25%): 8/2/0.5). The free base was crystallized as the hydrochloride from ethyl acetate giving the title compound in 350 mg yield. M.p. 232–235° C. (Compound 5).

EXAMPLE 3

(Z) 3-(3-methyl-5-isoxazolyl)methylene-1-methylpiperidine oxalate and (E) 3-(3-methyl-5-isoxazolyl)methylene-1-methylpiperidine oxalate.

To a solution of 3-methyl-5-trimethylsilylmethyl-isoxazole (J. Organomet. Chem. 195,3,1980,275–284) (2.0 g., 12 mmol) in dry tetrahydrofuran (25 ml) cooled to −78° C., butyllithium (1.64 M in hexane, 12 mmol) was added dropwise. The reaction mixture was stirred at −78° C. for 2 hours. A solution of 1-methyl-piperidin-3-one (1.35 g, 12 mmol) in dry tetrahydrofuran (20 ml) was added dropwise at −78° C. The reaction mixture was warmed to 4° C. and kept at this temperature overnight. The reaction mixture was evaporated to half volume in vacuo and water (25 ml) was added. The water phase was extracted with ethylacetate (3×25 ml). The organic extracts were dried over magnesiumsulfate and evaporated. The crude compound was separated by column chromatography on silica (eluent: ethylacetate/methanol/ammoniumhydroxide, 25% in water: 3/1/0.5%). The first fractions contained the (Z) 3-(3-methyl-5-isoxazolyl)methylene-1-methylpiperidine which was crystallized as the oxalate salt in 450 mg yield. Compound 1 Mp 163–64° C. The next fractions contained nonseparated Z and E isomer in 1.3 g yield. The last fractions contained pure (E) 3-(3-methyl-5-isoxazolyl) methylene-1-methylpiperidine, which was crystallized as the oxalate salt in 120 mg yield. Compound 6. Mp 214–15° C.

In the same manner the following compounds were prepared:

(Z) 3-(3-methyl-5-isoxazolyl)methylene-1-methylpyrolidine oxalate, compound 8, and (E) 3-(3-methyl-5-isoxazolyl)methylene-1-methylpyrrolidine oxalate, compound 9, starting form 1-methyl-pyrrolidin-3-one (J. Amer. Chem. Soc., 55, 1933, 1233–1241) and 3-methyl-5-trimethylsilylmethyl-isoxazole.

EXAMPLE 4

(Z) 3-(3-methyl-5-isoxazolyl)methylene-piperidine hydrochloride and (E) 3-(3-methyl-5-isoxazolyl) methyl ene-piperidine hydrochloride.

To a solution of 3-(3-methyl-5-isoxazolyl)methylene-1-methylpiperidine (1.3 g, 6.5 mmol) in toluene (30 ml ) cooled to 0° C., 1-chloroethyl chloroformate (1.1 ml, 10 mmol) was added. The reaction mixture was heated at reflux for 5 hours. The solvent was evaporated in vacuo, and methanol (20 ml) was added. The reaction mixture was heated at reflux for 1 hour, then evaporated in vacuo. The crude material was purified by column chromatogaphy on silica (eluent: ethylacetate/methanol/ammoniumhydroxide, 25% in water: 3/1/0.5%). The first fractions contained the (Z) 3-(3-methyl-5-isoxazolyl)methylenepiperidine which was crystallized as the hydrochloride salt from ethylacetate in 120 mg yield. Compound 5 Mp 232–35° C. The next fractions contained (E) 3-(3-methyl-5-isoxazolyl) methylene-piperidine, which was crystallized as the hydrochloride salt from ethylacetate in 190 mg yield.Compound 7. Mp 219–20° C.

EXAMPLE 5

3-(3-methyl-5-isoxazolyl)methyleneazetidine hydrochloride.

To a solution of 3-methyl-5-trimethylsilylmethyl-isoxazole (J. Organomet. Chem. 195,3,1980,275–284) (1.69 g., 10 mmol) in dry tetrahydrofuran (40 ml) cooled to −78° C., butyllithium (2.5 M in hexane, 10mmol) was added dropwise. The reaction mixture was stirred at −78° C. for 1 hour. A solution of N-benzhydrylazitidin-3-one (J. Heterocycl. Chem. 31, 271, 1994) (2.50 g, 10.5 mmol) in dry tetrahydrofuran (20 ml) was added dropwise at −78° C. The reaction mixture was stirred at −70° C. for 2 hours. The reaction mixture was quenched with 1 N Hydrochloric acid solution. The precipitated crystalline material was filtered. The crystals were suspended in water (50 ml) and the water suspension made alkaline with solid potassiumcarbonate. The free base was extracted with methylenchloride (3×75 ml). The combined organic extracts were dried over magnesiumsulfate and evaporated. The crude material was redissolved in methylenchloride (20 ml) and cooled to 0° C. 1 -Chloroethyl chloroformate (0.815 g, 5.7 mmol ) was added and the reaction mixture was stirred for 20 min. The reaction mixture was evaporated in vacuo, then redissolved in methanol (20 ml). The reaction mixture was heated at reflux for 1 hour, and evaporated in vacuo. The crude material was suspended in ether and the precipitated crystals filtered, giving the title compound in 370 mg yield. Compound 10. Mp 168–69° C.

We claim:

1. A compound of formula I

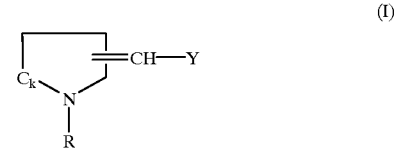

(I)

wherein k is 0, 1, 2 or 3; and R is hydrogen, $C_{1-6}$-alkyl or $C_{3-6}$cycloalkyl; and
wherein Y is

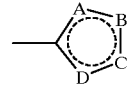

wherein —A—B—C—D— is selected from $=C(R^1)$—O—N$=C(R^2)$—, $=C(R^1)$—S—N$=C(R^2)$—, $=C(R^1)$—N$=C(R^2)$—O—, $=C(R^1)$—C($R^2)=$N—O—, $=C(R^1)$—N$=C(R^2)$—S—, $=C(R^1)$—C($R^2)=$C($R^3$)—S—, $=C(R$ )—C($R^2)=$N—S—, —C($R^1)=$C($R^2$)—O—C($R^3)=$, —C($R^1)=$C($R^2)$—S—C($R^3)=$, —N($R^4$)—N$=C(R^1)$—C($R^2)=$, $=N$—N($R^4$)—C($R^1)=$C($R^2)$—, $=N$—O—C($R^1)=$C($R^2)$—, $=N$—S—C($R^1)=$C($R^2)$—, —N($R^1)$—C($R^1)=$N—C($R^2)=$, $=C(R^1)$—N($R^4$)—N$=C(R^2)$—, $=N$—C($R^1)$—O—C($R^2)=$, —N$=C(R^1)$—S—C($R^2)=$, $=N$—C($R^1)=$C($R^2)$—N($R^4$)—, $=N$—C($R^1)=$C($R^2)$—O—, $=N$—C($R^1)=$C($R^2)$—S—, —N($R^4$)—N$=N$—C($R^1)=$, $=N$—N($R^4$)—N$=C(R^1)$—, —N$=N$—N($R^4$)—C($R^1)=$, —N($R^4$)—N$=C(R^1)$—N$=$, $=N$—N($R^4$)—C($R^1)=$N—, $=N$—N$=C(R^1)$—N($R^4$)—, $=N$—O—N$=C(R^1)$—, $=N$—N$=C(R^1)$—O—, —N$=N$—C($R^1)$—O—N$=$, $=N$—O—N$=C(R^1)$—, ($R^1)=$N—O—, $=N$—N$=C(R^1)$—S—, $=N$—S—N$=C(R^1)$—, $=N$—C($R^1)=$N—S—, —N$=C(R^1)$—S—N$=$, —N($R^4$)—N$=N$—N$=$, $=N$—N($R^4$)—N$=N$—; and $R^1$, $R^2$ and $R^3$ independently are hydrogen, halogen, —NO$_2$, —CN, —NR$^5$R$^6$, —OR$^7$, —SR$^{3,}$ —COOR$^9$, —SOR$^1$, —SO$_2$R$^{11}$, —SO$_3$R$^{12}$, C$_1$—alkyl optionally substituted with one, two or three fluorine atoms, C$_{2-6}$-alkenyl, C$_{2-6}$-alkynyl, C$_{3-6}$-cycloalkyl, —R$^3$—O—R$^{14}$ or —R$^{15}$—S—R$^{16}$, and R$^4$ is C$_{1-6}$-alkyl, C$_{2-6}$-alkenyl, C$_{2-6}$-alkynyl, C$_{3-6}$-cycloalkyl, —R$^{17}$—O—R$^{18}$ or —R$^{19}$—S—R$^{20}$, wherein R$^5$ and R$^6$ independently are hydrogen, C$_{1-6}$-alkyl, C$_{2-6}$—alkenyl or C$_{2-6}$-alkynyl and wherein R$^7$ R$^8$, R$^9$, R$^{10}$, R$^{11}$, R$^{12}$, R$^{14}$, R$^{16}$, R$^{18}$ and R$^{20}$ independently are hydrogen, C$_{1-6}$-alkyl, C$_{2-6}$-alkenyl, C$_{2-6}$-alkynyl or C$_{3-7}$-cycloalkyl and wherein R$^{13}$, R$^{15}$, R$^{17}$ and R$^{19}$ independently are C$_{1-6}$-alkylene, C$_{2-6}$-alkenylene or C$_{2-6}$-alkynylene; or a pharmaceutically acceptable salt thereof.

2. A compound according to claim 1 of formula I$a$

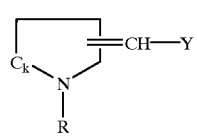

(I$a$)

wherein A—B—C—D is selected from =C(R$^1$)—C(R$^2$)=N—O—, =C(R$^1$)—C(R$^2$)=N—S—, =N—O—C(R$^1$)=C(R$^2$)—, and =N—S—C(R$^1$)=C(R$^2$)—, wherein R$^1$ and R$^2$ have the meanings defined in claim 1.

3. A compound according to claim 1, wherein the compound is selected from the following:

(Z)—3—(3—Methyl—5—isoxazolyl)methylene—1—methylpiperidine, (E) 3—(3—methyl—5—isoxazolyl)methylene—1—methylpiperidine, (E) 3—(3—methyl—5—isoxazolyl)methylene—1—methylpyrrolidine, (Z) 3—(3—methyl—5—isoxazolyl)methylene—1—methylpyrrolidine, 4—(3—Methyl—5—isoxazolyl)methylene—1—methylpiperidine, (Z)—3—(3—Methyl—5—isoxazolyl)methylenepiperidine, (E)—3—(3—Methyl—5—isoxazolyl)methylenepiperidine, and 3—(3—methyl—5—isoxazolyl)methyleneazetidine; or a pharmaceutically acceptable salt thereof.

4. A method of preparing a compound according to claim 1, comprising a) reacting a compound of formula II:

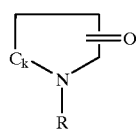

(II)

wherein k is as defined in claim 1, with a phosphorus ylide of formula III or a phosphonate of formula IV

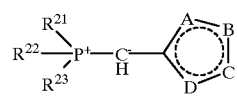

III

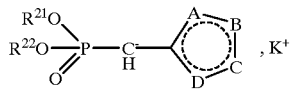

IV wherein R$^{21}$, R$^{22}$ and R$^{23}$ independently are C$_{1-6}$-alkyl, aryl or aralkyl and —A—B—C—D—has the meaning defined in claim 1, to give a compound of formula I; or b) reacting a compound of formula II with a compound of formula V

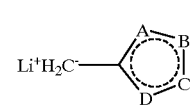

(V)

wherein —A—B—C—D—has the meaning defined in claim 1, followed by a dehydration to give a compound of formula I; or c) reacting a compound of formula II with a compound of formula VI

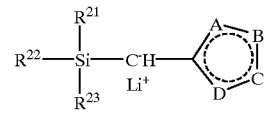

(VI)

wherein R$^{21}$, R$^{22}$ and R$^{23}$ have the meanings defined above, to give a compound of formula I; or d) reacting a compound of formula II with a compound of formula VII

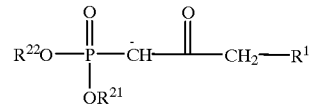

(VII)

wherein R$^1$ has the meaning defined in claim 1 and R$^{21}$ and R$^{22}$ have the meanings defined above, to give a compound of formula VIII (VIII)

followed by reaction with dimethylformamide dimethylacetale and cyclization with hydroxylamine to give a compound of formula IX

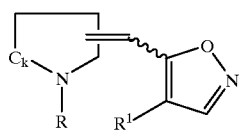

(IX)

wherein R and R$^1$ have the meanings defined in claim 1.

5. A pharmaceutical composition comprising as active component a compound according to claim 1 together with a pharmaceutically acceptable carrier or diluent.

6. The pharmaceutical composition according to claim 5 in the form of an oral dosage unit or parenteral dosage unit.

7. The pharmaceutical composition according to claim 6, wherein said dosage unit comprises from about 1 to about 100 mg of the compound claim 1.

8. A method of treating a central nervous system ailment related to malfunctioning of the nicotinic cholinergic system in a subject in need of such treatment comprising administering to said subject an effective amount of a compound according to claim 1.

9. A method of treating Alzheimer's disease, Parkinson's disease, Tourette's syndrome, ulcerative colitis, obesity, gastrointestinal disorders or severe pain, preferably obesity, in a subject in need of such treatment comprising administering to said subject an effective amount of a compound according to claim 1.

10. A method of treating or preventing withdrawal symptoms caused by cessation of chronic or long term use of tobacco products comprising administering to a subject in need thereof an effective amount of a compound according to claim 1.

* * * * *